US005696094A

United States Patent [19]

Yamashita

[11] Patent Number: 5,696,094
[45] Date of Patent: Dec. 9, 1997

[54] CONTROL OF SOIL BORNE PESTS AND PATHOGENS

[76] Inventor: Thomas T. Yamashita, 281 W. Audubon, Fresno, Calif. 93711

[21] Appl. No.: 656,073

[22] Filed: May 31, 1996

Related U.S. Application Data

[63] Continuation of Ser. No. 297,488, Aug. 29, 1994, abandoned, which is a continuation-in-part of Ser. No. 572,492, Aug. 23, 1990, Pat. No. 5,582,627, and a continuation-in-part of Ser. No. 855,079, Mar. 23, 1992, abandoned.

[51] Int. Cl.$^6$ .......................... A61K 31/70; A01N 43/04
[52] U.S. Cl. .......................... 514/22; 514/54; 424/DIG. 8
[58] Field of Search .................. 514/22, 54; 424/DIG. 8

[56] References Cited

PUBLICATIONS

Sitaramaiah and Singh, "Effect of Organic Amendment on Phenolic Content of Soil and Plant and Response of Meloidogyne Javanica and Its Host to Related Compounds," Plant and Soil (1978), 50:671–679.

Alam et al., "Mechanism of Control of Plant Parasitic Nematodes as a Result of the Application of Organic Amendments to the Soil. V–Role of Phenolic Compounds," Indian F. Nematol. (1979), 9:136–142.

Sitaramaiah and Pathak, "Effect of Growth Regulators, Phenolics and an Aromatic Acid on Root–Knot Severity (Meloidogyne Incognita and M. Javanica on Tomato)," Zeitschrift Für Pflanzenkrankheiten und Pflanzenschutz Journal of Plant Diseases and Protection (1981), 88:651–654.

Mahajan et al., "Nematicidal Activity of Some Phenolic Compounds Against Meloidogyne Incognita," Revue Nématol (1985), 8:161–164.

Balaji and Kannan, "Impact of Different Phenolic Compounds on Hatchability of Meloidogyne Incognita," Geobios (1988), 15:143–144.

Maheshwari and Anwar, "Nematicidal Activity of Some Phenolics on Root Knot, Growth and Yield of Capsicum Frutescens cv. California Wonder," J. Phytopathology (1990), 129:159–164.

Mahmood and Siddiqui, "Effect of Phenolics on the Growth of Tomato and Reproduction of Rotylenchulus Reniformis," Nematol. Medit. (1993), 21:97–98.

Rodriguez–Kabana, et al., Use of Mixtures of Urea and Blackstrap Molasses For Control of Root–Knot Nematodes In Soil, Nematropica vol. 10, No. 1, 1980, pp. 38–44.

Huebner, Rodriguez–Kabana, et al., Hemicellulosic Waste and Urea For Control of Plant Parasitic Nematodes: Effect On Soil Enzyme Activities, Nematropica vol. 13, No. 1, 1983, pp. 37–54.

Muller and Gooch, Organic Amendments In Nematode Control, An Examination of the Literature, Nematropica vol. 12, No. 2, 1982, pp. 319–326. Pages are missing from the Muller and Gooch paper. It is believed that the Abstract is sufficient.

Rodriguez–Kabana, et al., Biological Control of Nematodes: Soil Amendments and Microbial Antagonists, Plant and Soil 100, 1987, pp. 237–247.

Literature Review, The Effects of Carbon and Nitrogen Amendments On Nematode Populations, Dec. 20, 1993, pp. 2–4.

*Primary Examiner*—John W. Rollins
*Attorney, Agent, or Firm*—Fish & Richardson P.C.; Bret E. Field

[57] ABSTRACT

A method of controlling soil borne pests and pathogens, e.g., nematodes in which a predisposition material is incorporated in the soil which predisposes the pests or pathogens by weakening their resistance to attack by soil microbes. The predisposing material may be a lignosulfonate or other organic material which penetrates the cuticle of the pests or pathogens and renders them more amenable to attack by soil microbes. Preferably the predisposition material is accompanied by nutrient material such as a sugar, which may be a natural accompaniment of the predisposition material as in the case with lignosulfonates and/or which may be added. Preferably also the predisposition material is accompanied by macronutrients such as nitrogen and phosphorus macronutrients, also micronutrients and vitamin/co-factor.

12 Claims, No Drawings

CONTROL OF SOIL BORNE PESTS AND PATHOGENS

This is a continuation of application Ser. No. 08/297,488 filed Aug. 29, 1994, now abandoned, which is a continuation-in-part of the following applications: Ser. No. 07/572,492 entitled DETOXIFICATION OF SOIL filed Aug. 23, 1990, now U.S. Pat. No. 5,582,627, and Ser. No. 07/855,079 entitled COMPOSITION AND METHOD OF TREATING SOIL filed Mar. 23, 1992, now abandoned.

BACKGROUND OF THE INVENTION

This invention relates to a method and to compositions for the control of soil borne pests and pathogens of the animal kingdom.

Nematodes are an example of soil borne pathogens and pests which are the subject of this invention. Nematodes, e.g., the species *Meloidogyne incognita, Pratylenehus penetrans, Criconemella xenoplax, Xiphinema americanum, Meloidogyne javanica, M. hapla, Pratylenchus vulnus, Paratylenchus mineus, Tylenchulus semipenetrans, Helicotylenchus spp., Nacobbus aberrans, Heterodera spp., Ditylenchus spp., Xiphinema index, Longidorus spp., Rhadopholus spp.*, are widely prevalent in soil and are harmful to crops grown in the soil. For example crops such as [field crops]: sugar beets, alfalfa, corn, cotton, wheat, safflower, sunflower, flax, soybeans, beans, peas, milo, barley, rape; [vegetable crops]: lettuce, tomato, carrots, beets, broccoli, spinach, cabbage, pepper, cucumber, onions, radish, potato, taro, pumpkins; [fruit and nuts crops]: almonds, peaches, plums, pistachios, walnuts, apples, cherries, grapes, kiwi, fajoa, banana, cacao, guava, filberts, macadamia, oranges, lemons, grapefruit, nectarines, strawberries, raspberries, blueberries, cranberries; [ornamentals]: pine, redwood, fir, larch, birch, elm, alder, aspen, ash, flowering pear, flowering plum, jasmine, boxwood, rose, chrysanthemum, carnation, rhododendron, azalea, camellias, nandina, juniper, bluegrass, rye grass, fescue, ivy, are adversely affected by nematodes in the soil.

The soil borne pests and pathogens to which this invention is applicable also include arthropods, e.g.,:

Insects

The order Homoptera such as Grape Phylloxera (*Daktulosphaira vitifoliae*); Strawberry Root Aphid (*Aphis forbesi*); Sugar Beet Root Aphid (*Pemphigus betae*); and Woolly Apple Aphid (*Eriosoma lanigerum*).

The order Coleoptera such as Strawberry Root Weevil (*Brachyrhinus ovatus*); White Grubs (many species of Phyllophaga, Family Scarabacidae); Japanese Beetle (*Popiliia japonica*); and Wireworms (many species of family Elateridae).

The order Lepidoptera such as Cutworms (many species of the family Noctuidae); and Armyworms (*Pseudaletia unipuncta*).

The order Diptera such as Root Maggots (many species of family Anthomyiidae).

Mites

Soil mites (various species of order Acarina).

Presently toxic materials are incorporated in the soil to eradicate such pathogens and pests or to diminish their harmful effects. For example, methyl bromide is commonly injected into the soil on which various crops are to be grown, such as strawberries, fruit and nut trees, vines, onions, kiwi, seed carrots. Other fumigants include: Telone (1, 3-dichloropropene), Vapam (metam-sodium), Vorlex (methyl isothiocyanate), carbon disulfide, chloropicrin, ethylene dibromide, dazomet, nemacur, furadan, vydate, temik, and mocap.

Such methods are expensive and they introduce the hazard of toxic materials escaping into the environment or being harmful to workers.

In a paper published in 1983 by Huebner and others, in the Journal Nematropica, Vol. 13, pgs. 37–54, the use of urea as a nematocide is described. The urea hydrolyzes to ammonia which is the effective nematocide. The urea is used in amounts that are phytotoxic. To inhibit this phytotoxic effect hemicellulosic waste is added to soil along with the urea. The hemicellulosic waste is that resulting from alkaline and bisulfite treatment of wood to release cellulose.

The method of Huebner, as stated above, uses urea as the active nematocide and hemicellulosic waste as an inhibitor of phytotoxicity. The amounts of both urea and hemicellulosic waste applied to the soil by Huebner are such that the urea is phytotoxic (but its use is said to be justified because of its nematocidal effect) and both the urea and the hemicullulosic waste are expensive in the amounts used.

OBJECTS OF THE INVENTION

It is an object of the invention to provide methods using compositions which are non-toxic or relatively non-toxic to human beings but which are effective to control infestation of the soil by pests and pathogens.

It is a further object of the invention to provide compositions for application to soil, and rates of application of such compositions to soil, which are not phytotoxic with respect to the crops grown in the soil (or which have at most an acceptable level of phytotoxicity) but which are effective to eliminate, or greatly reduce the phytotoxicity of soil pathogens and pests.

The above and other objects of the invention will be apparent from the ensuing description in the appended claims.

SUMMARY OF THE INVENTION

In accordance with the invention soil contaminated or likely to be contaminated with soil borne pests or pathogens of the animal kingdom is treated with a substance which is relatively non-toxic and which functions when it comes into contact with pests or pathogens in the soil to be absorbed through the cuticles and to so affect the pseudocoelomic fluid as to render the pests or pathogens more amenable to attack by soil microbes such as soil fungi and soil bacteria.

Preferably this material is accompanied by a nutrient medium which serves to promote the growth of soil microbes such as fungi and soil bacteria. It also may be accompanied by the introduction of soil microbes which are grown separately from the soil being treated and which are known to be effective in controlling pests and pathogens.

DETAILED DESCRIPTION OF THE PREFERRED EMBODIMENTS

The material used to inactivate or destroy the pests or pathogens is preferably a soluble lignosulfonate, e.g., calcium, potassium, sodium or ammonium lignosulfonate. Lignosulfonate is a product of the pulping of wood to produce pulp for the manufacture of paper. Lignin itself is known to be a complex randomly cross-linked polymer in which phenyl propane derivatives are the building blocks.

See, for example the product brochure: "Lignosulfonate Products," Georgia Pacific Publication, 1754 Thorne Road, Tacoma, Wash. 98421. This lignin is found in woody tissues, e.g., in soft woods such as pines. It is extracted from wood by a sulfite liquor and exists in the form of a sulfonate such as the calcium, ammonium, sodium or potassium sulfonate which are water soluble. A calcium lignosulfonate of that company which is suitable is described in the company's literature as follows:

A 50% aqueous solution of high purity derived from soft wood and as having the following specification:

CHEMICAL DESCRIPTION

| | |
|---|---|
| Total solids, % | 50.0 |
| Calcium lignin sulfonate, % | 40.0 |
| Methoxyl, % | 4.2 |
| Reducing sugars (as glucose), % | 3.6 |
| Calcium (soluble), % | 2.5 |
| Sodium, % | 0.5 |
| Insolubles (CaSO$_4$ 2H$_2$O, %) | 1.5–2.0 |
| pH of 10% solution | 5.5 |
| PHYSICAL PROPERTIES | |
| Specific gravity (liquid, 25°/15° | 1.252 |
| Gallon weight, lbs | 10.4 |
| Heat of combustion, BTU/lb solids | 8100 |
| Viscosity, cp at 25° C. | 700 |

It is believed that the sulfonates, when incorporated in soil infected with pests or pathogens, e.g., nematodes, penetrate the cuticle of the organisms and enter the pseudocoelomic fluid of the organisms where it adversely affects the enzymes of the organisms. This in turn is believed to weaken the organisms resistance to invading soil bacteria leading to the destruction or inactivation of the organisms.

Whatever the mechanism I have discovered that lignosulfonate does in fact greatly mitigate or completely destroy the pathogenic effect of soil pests and pathogens.

The lignosulfonate may be dissolved in water which is then used by way of any of several methods for application to soil, e.g., by sprinkling, by drip methods, by field irrigation, by spraying the soil or by injection into the soil followed by irrigation. The lignosulfonate may also be applied in dry form as by aerial dusting followed by irrigation to dissolve the lignosulfonate and cause it to penetrate the soil. The lignosulfonate may be applied uniformly over an area or it may be applied selectively in the vicinity of plants, seeds or seedlings. It may also be applied in pelletized form.

The lignosulfonate, produced as a byproduct of wood pulping, contains also certain nutrients, e.g., sugars which are useful nutrients for soil bacteria which in turn penetrate and destroy the soil pests and pathogens exposed to the lignosulfonate. It is advantageous, however, to supplement the lignosulfonate directly, or by adding to the soil treated with lignosulfonate, a more complete nutrient material comprising nitrogen and phosphorus macronutrients, also various other macro- and micronutrients together with a vitamin/co-factor such as yeast extract.

It may also be advantageous to supplement the naturally occurring soil bacteria with added bacteria or other microbes which effectively complement the action of the lignosulfonate.

Instead of lignosulfonates as the penetrant material, other materials may be used such as [1] aromatic amino acids (e.g., tyrosine, phenylalanine, tryptophan, shikimic acid); [2] miscellaneous simple phenols and sister compounds (e.g., chlorogenic acid, caffeic acid, cinnamic acid, coumaric acid, catechuic acid, ferulic acid, chorismic acid, quinic acid, gallic acid, gallotannins, scopeletin, dicoumarol, preocenes, phytoalexins such as orchinol, phaseolin, pisatin, isocoumarin); [3] cignin alcohols (e.g., conferyl, sinapyl, p-coumaryl); [4] flavanoids (e.g., cyanidin, anthocyanidin, pelargonidin, delphinidin, malidin, peonidin, petunidin); [5] flavonols and flavones; [6] betalains (e.g., betacyanin, betalain, betaxanthin) and [7] alkaloids (e.g., caffeine, nicotine, theobromine); [8] limonene (1-Methyl-4-(1-Methylethenyl) cyclohexene; p-mentha-1, 8-diene.

The following specific examples serve further to illustrate the practice and advantages of the invention.

EXAMPLE 1

This describes a preliminary test to show the effectiveness of lignosulfonate for the intended purpose. In this and in Examples 2 to 5 the lignosulfonate was the primary "predisposing agent" to microbial colonization. It also served as a source of carbon for microbial growth. Indirectly, the mineral-complexing properties of lignosulfonate helped to release more mineral from the soil for microbial growth requirements. In Examples 1 to 5 it was the Georgia Pacific lignosulfonate described above.

Mixed stages of three nematode species were exposed 24 hours to various concentrations of lignosulfonate in shallow 50 ml beakers. Following exposure nematodes were inspected for activity level using touch response:

| | ppm Concentration | | | | |
|---|---|---|---|---|---|
| Nematode | 0 | 1000 | 2000 | 4000 | 8000 |
| M. incognita (J2 larvae) | 455/455 | 298/476 | 112/515 | 25/489 | 1/505 |
| P. penetrans (mixed stages) | 471/471 | 335/486 | 183/510 | 14/502 | 0/479 |
| C. xenoplax (mixed stages) | 358/358 | 312/488 | 117/490 | 23/413 | 0/425 |

Counts are the number of active nematodes per total of 4 beakers per treatment. The figure preceding the slash mark is the count of surviving nematodes while the figure following the slash mark is the original number of nematodes.

EXAMPLE 2

Potted Plant Tests

A mixture of white, washed sand plus coarse river sand was mixed at a v/v ratio of 1:1. Rutgers tomato cuttings were started (1 each) in 6" clay pots using the sand mixture medium. Cuttings were allowed to develop for 1 month. Kentucky Wonder bush beans were planted (1 each) in another set of 6" clay pots and allowed to develop for 1 month. A third set of pots were planted to rose cuttings (variety: Peace) and allowed to develop for 1.5 months. All plants were watered daily with ½ strength Hoagland's Solution. Tomato plants were inoculated with an aliquant of ‾2,000 J2 *Meloidogyne incognita* larvae per pot. Beans were inoculated with ‾2,000 mixed stage larvae of *Pratylenchus penetrans* per pot. Pots with rose plants were inoculated with ‾2,000 mixed stage *Criconemella xenoplax* per pot. All nematodes were delivered in 20 ml of suspension with 4 ml placed into each of 5, 1" deep holes spaced evenly about the plant. Holes were covered with the sand mixture and lightly watered to seal air pockets. On the day following inoculation pots were treated with 4000 ppm (ca. 150 gpa) of calcium lignosulfonate solution (drenched to run-off) and again on the next day with 500 ml of the same solution. On the second treatment, pots were underlain with trays to catch run-off. All pots were left unwatered for an additional 24 hour before resuming watering with ½ strength Hoagland's solution (with trays removed). Nematodes and plants were allowed to grow for an additional 45 days before processing for gall and nematode counts. Controls were handled the same but treated with only ½ strength Hoagland's Solution. The initials M.i., P.p. and C.x. indicate *Meloidogyne incognita, Pratylenchus penetrans* and *Criconemelle xenoplax*, respectively. Similar in nomenclature is used throughout.

|             | Replications |      |      |      |      |      |
|-------------|------|------|------|------|------|------|
| Treatment   | 1    | 2    | 3    | 4    | 5    | Mean |
| M.i. Control | 234 | 156  | 256  | 176  | 279  | 220  |
| M.i. Treated | 3   | 10   | 5    | 0    | 5    | 5    |
| P.p. Control | 3350 | 3530 | 4050 | 2980 | 3650 | 3512 |
| P.p. Treated | 13  | 7    | 2    | 19   | 2    | 9    |
| C.x. Control | 1580 | 1740 | 1380 | 1550 | 1900 | 1630 |
| C.x. Treated | 0   | 11   | 3    | 0    | 8    | 4    |

1 gph = gallons per acre
Counts for *M. incognita* represent galls; all other counts represent recovered nematodes. *P. penetrans* were recovered from both sand and roots, *C. xenoplax* from sand only.
Side Observation of Experiment 2 - Occasionally, bodies of nematodes were found heavily ramified with hyphae of fungi and/or dead with cleared internal structures oftentimes teeming with protozoa or bacteria. A casual examination of the soil microflora revealed predominately fungi of the genera Trichoderma and Penicillium.

EXAMPLE 3

This example illustrates the role of soil microbiota in conjunction with the lignosulfonate.

White sand and river sand were, again, used (1:1 v/v) and potted into 3" diameter clay pots. Half of the pots were autoclaved for 3 hours to sterilize the sand mixture. Half of the pots were left unsterilized. A portion of nematodes being used in the "sterile" treatments were surface sterilized by 2 hours exposure to a solution of 1000 ppm streptomycin sulfate plus 500 ppm cycloheximide. All surface sterilized nematodes were then washed with three repeated drenches of sterilized tap water before placing into agitated flasks for viability observations. Sterilized pots were kept semi-sterilized by placing them into sterilized "crispers" which minimized outside contamination. These sterilized pots were inoculated with 1000 surface sterilized nematodes (M. incognita, J2 stages; P. penetrans, mixed stages; C. xenoplax, mixed stages). The unsterilized pots were inoculated with like numbers of nematodes not receiving surface sterilization treatments. All pots were wetted with sterilized tap water and the nematodes allowed to distribute in the sand mixture for 24 hours. Following 24 hours, half of the sterilized pots were drenched with 4000 ppm of a calcium lignosulfonate solution (250 ml; which had been sterilized by passage through coarse silicate filters and then 0.2 micron millipore filters). All pots were underlain with sterilized dishes to catch run-off. The other half of the sterilized pots were drenched with 50 ml of sterilized ½ strength Hoagland's Solution. Unsterilized pots were treated in a like manner but with unsterilized lignosulfonate solution (treated) and ½ strength Hoagland's Solution (control). All pots were kept in crispers and periodically aerated (all pots maintained at ambient room temperature of 25° C.). Nematode counts, viability tests and/or degree of inactivity were made 30 days following treatment.

|                 | Replications |     |     |     |     |      |
|-----------------|------|-----|-----|-----|-----|------|
| Treatment       | 1    | 2   | 3   | 4   | 5   | Mean |
| M.i. Sterile (C) | 223 | 215 | 256 | 331 | 227 | 250  |
| M.i. Sterile (T) | 175 | 188 | 159 | 126 | 182 | 166  |
| M.i. Nonster (C) | 208 | 216 | 223 | 237 | 281 | 233  |
| M.i. Nonster (T) | 13  | 7   | 10  | 5   | 3   | 8    |
| P.p. Sterile (C) | 187 | 235 | 265 | 232 | 206 | 225  |
| P.p. Sterile (T) | 145 | 167 | 198 | 134 | 109 | 151  |
| P.p. Nonster (C) | 183 | 190 | 245 | 231 | 243 | 218  |
| P.p. Nonster (T) | 15  | 11  | 7   | 3   | 5   | 8    |
| C.x. Sterile (C) | 221 | 289 | 304 | 323 | 310 | 289  |
| C.x. Sterile (T) | 109 | 87  | 125 | 165 | 171 | 131  |
| C.x. Nonster (C) | 281 | 305 | 315 | 286 | 256 | 289  |
| C.x. Nonster (T) | 2   | 4   | 10  | 7   | 7   | 6    |

NOTE:
Treatments under non-sterilized conditions had significant mortality. It appears quite obvious that the initial weakening effect of the lignosulfonate solution in conjunction with the presence of invading microbes is primarily responsible for nematode mortality. C = Control, T = Treatment.

Although several of the nematodes survived the treatment under sterilized conditions, survivors looked sluggish with cleared intestinal tracts. Had soil microbiota been present and active, many of these would have succumbed completely to the treatment.

EXAMPLE 4

This example compares the effects of different microbial species. It illustrates the fact that lignosulfonate with mixed species of fungi and soil bacteria provide better results than lignosulfonate alone or with fungi alone or with soil bacteria alone.

Mixed stages of *C. xernoplax* were surface sterilized and inoculated into sterilized pots, as outlined in Example 3. These pots were inoculated as follows:

(a) Sterilized lignosulfonate solution (4000 ppm) [TS]

(b) Sterilized lignosulfonate solution +
  (1) Mixed species of soil microbiota isolated from soil and grown on yeast extract nutrient agar (cultures grown for 7 days on 100 mm dia plates were washed with 250 ml of the lignosulfonate solution and this solution poured into treatment pots); Species identified included: [TM]
   [Fungi: *Penicillium sp., Trichoderma sp., Mucor sp., Cladosporium sp.*; $^{-10}$ 6th colony forming units/ml]
   [Bacteria: *Pseudomonas fluorescens, Arthrobacter sp.*; $^{-10}$ 8th cfu's/ml]
  (2) Mixed species of soil fungi isolated from soil and grown on acidified potato dextrose agar: [TF]
   [Fungi: *Penicillium sp., Trichoderma sp., Mucor sp., Cladosporium sp.*; $^{-10}$ 7th cfu's/ml]
  (3) Mixed species of soil bacteria isolated from soil and grown on yeast extract nutrient agar: [TB]
   [Bacteria: Pseudomonas fluorescens, Arthrobacter sp.; 10 8th cfu's/ml]

(c) Control treatment consisting of sterilized ½ strength Hoagland's Solution [CC]

(d) Control treatment consisting of sterilized ½ strength Hoagland's Solution+mixed species of soil microbiota as in b-1, above; (similar concentration as in b-1 above [CM]

|            |     |     | Replications |     |     |      |
| Treatments | 1   | 2   | 3   | 4   | 5   | Mean |
| --- | --- | --- | --- | --- | --- | --- |
| Control [CC] | 325 | 301 | 296 | 340 | 335 | 319 |
| Control [CM] | 316 | 328 | 333 | 290 | 267 | 307 |
| Treat [TS] | 146 | 127 | 106 | 128 | 158 | 133 |
| Treat [TM] | 9 | 13 | 5 | 11 | 16 | 11 |
| Treat [TF] | 14 | 29 | 17 | 33 | 19 | 22 |
| Treat [TB] | 76 | 53 | 72 | 49 | 81 | 66 |

All pots were initially inoculated with ~500 mixed stages of C. xenoplax.

EXAMPLE 5

This example indicates the mechanism of lignosulfonate+ mixed soil microbes (as in Example 4).

Dead but intact nematodes from the above Example 4 which were treated with "Mixed Soil Microbes" were gently washed successively (5 repeated washings) and plated onto microbial media plates (yeast extract nutrient agar and acidified potato dextrose agar). The predominately recovered microbes were fungi. Thus, it is believed that the weakened state of the nematode, initiated by lignosulfonate treatments, predisposes the nematode to initial attack by various species of fungi. Death and incipient degradation of the cadaver then opens avenues for invasion by several bacterial species. It appears as though the effects of the "total" soil microflora are more effective than any one group alone. Secondly, results from the "Treated, Unsterilized" trials in Example 3 suggest that additional microbes on the surface of nematodes may also contribute to mortality.

EXAMPLE 6

Melon Study

Method

A melon field had been treated with Treflan. The melon plants were young seedlings. There was visible damage from Treflan residue, the roots of seedlings typically bent near the soil line and swollen for 3"–6" down towards the tap root. Secondly, nematode galls from diagnosed populations of *Meloidogyne incognita* (Root—Knot Nematode) were numerous averaging 16 galls per seedling (number of plants examined=20). The composition of Table 1 was shanked in at 30 gallons/acre with spades on each side of the seedling (approximately 8" on either side) at a depth of 3". Seedlings were irrigated via sprinklers to distribute the material into the root zone. One month following treatment plants were examined for top and root growth (shoot length and root girth), galling and/or stunting and root swelling and bending. Root growth was evaluated on a 0–5 scale (5=excellent).

Results were as follows:

|           |     |     | Replications |     |     |      |
| Treatment | 1   | 2   | 3   | 4   | 5   | Mean |
| --- | --- | --- | --- | --- | --- | --- |
| 1. Top Growth ||||||||
| Control | 13" | 15" | 17" | 14" | 15" | 15 |
| Treated | 38" | 27" | 39" | 43" | 45" | 38 |

Note:
Numbers represent length of longest vine per randomly selected plant.

|           |     |     | Replications |     |     |      |
| Treatment | 1   | 2   | 3   | 4   | 5   | Mean |
| --- | --- | --- | --- | --- | --- | --- |
| 2. Nematode Galling ||||||||
| Control | 25 | 32 | 27 | 41 | — | 32 |
| Treated | 18 | 13 | 15 | 19 | — | 16 |

Note:
Numbers represent galls per root (from nematode damage). Average gall counts at the start of the experiment was 16.

| 3. Root Evaluation |||||||
| --- | --- | --- | --- | --- | --- | --- |
| Control | 2 | 1 | 2 | 1 | 1 | 1.4 |
| Treated | 4 | 5 | 5 | 4 | 5 | 4.6 |

Note:
Numbers represent root evaluation ratings with a 0–5 scale and 5 = excellent status.

Treflan, a product of Elanco Chemical Company, is Trifluralin ($\alpha,\alpha,\alpha$-trifluro-2,6-dinitro-N,N-dipropyl-p-toluidine) 44.5% active ingredient applied at 2 pints/acre.

Table 1 referred to above, is as follows:

TABLE 1

| Component | % by wt of active ingredient | % by wt of component based on complete mix | Final concentration of active ingredient based on wt of complete mix |
| --- | --- | --- | --- |
| High Brix Cane or Beet Molasses | 50.0% Sugar | 32.0% | 16.0% Sugars |
| Calcium Lignosulfonate | 50.0% CaLignosulfonate | 32.0% | 16.0% CaLignosulfonate |
| Urea | 23.0% N | 5.0% | 1.7% total Nitrogen |
| $KNO_3$ | 13.9% N | 3.8% | |
| $KNO_3$ | 38.7% K | | 1.5% Potassium |
| $H_3PO_4$ | 23.7% P | 3.4% | 0.8% Phosphorus |
| $ZnSO_4$—$7H_2O$ | 36.0% Zn | 0.8% | 0.3% Zinc |
| $FeSO_4$—$7H_2O$ | 31.0% Fe | 0.8% | 0.3% Iron |
| $MnSO_4$—$H_2O$ | 28.0% Mn | 0.8% | 0.2% Manganese |
| Vitamin B Complex | — | 1.0% | 0.04% B-Cplx |
| Water (Tap) | — | 20.4% | |

EXAMPLE 7

In this example mites and aphids were the subjects of treatment and were present on the leaves of plants rather than in the soil. The effect was to stun the mites and aphids which dropped to the soil where, in normal field practice, they would be attacked by soil microbes.

The concentrate used (in diluted form) was that of Table 2 below. In this Table the first column indicates the active ingredient, e.g., carbon skeleton-energy in the case of molasses; nitrogen, potassium and calcium in the case of calcium nitrate-potassium nitrate-urea mix, etc.

The second column indicates the form in which the active ingredient was added, e.g., a mix of calcium nitrate, potassium nitrate and urea in the case of nitrogen; the third column indicates the percentage of active ingredient in each substance, e.g., 50% sugar in the case of molasses and 12% nitrogen in the case of calcium nitrate; the fourth column indicates the proportion of each source in the total concentrate, e.g., 67% molasses, and 3.4% phosphoric acid; and the last column indicates the percentage of active ingredient in the concentrate, e.g., 33.5% in the case of molasses and 1.10% in the case of nitrogen.

Calcium nitrate contributed nitrogen and calcium and potassium nitrate contributed potassium and nitrogen. The total nitrogen (contributed by calcium and potassium nitrates) and urea was 1.10%.

The term "CSE" or carbon skeleton-energy signifies a source of carbon skeleton and energy for plant metabolism.

TABLE 2

| CSE | Molasses High Brix | 50.0% sugar | 67.00% | 33.50% |
|---|---|---|---|---|
| Nitrogen | Ca(NO$_3$)2—4H$_2$O | 12.0% N | See below | |
| | KNO$_3$ | 13.9% N | See below | |
| | Urea | 23.0% N | 1.16% | 1.10% |
| Phosphorus | Phosphoric acid | 23.7% P | 3.40% | 0.80% |
| Potassium | KOH | 70.0% K | 1.06% | 1.50% |
| | KNO$_3$ | 38.7% K | 1.94% | |
| Calcium | Ca(NO$_3$)$_2$—2H$_2$O | 17.0% Ca | 4.69% | 0.80% |
| Magnesium | MgSO$_4$—H$_2$O | 9.9% Mg | 1.50% | 0.15% |
| Zinc | ZnSO$_4$ | 36.0% Zn | 0.35% | 0.13% |
| Iron | FeSO$_4$—2H$_2$O | 31.0% Fe | 0.41% | 0.13% |
| Manganese | MnSO$_4$—H$_2$O | 28.0% Mn | 0.44% | 0.13% |
| Copper | CuSO$_4$—5H$_2$O | 25.2% Cu | 0.08% | 0.02% |
| Boron | M$_3$BO$_3$ | 17.5% B | 0.09% | 0.02% |
| Molybdenum | Na$_2$MoO$_4$—H$_2$O | 39.7% Mo | 0.002% | 0.009% |
| Cobalt | CoSO$_4$—7H$_2$O | 20.8% Co | 0.03% | 0.01% |
| Vitamin-B Complex | Vitamin Premix | | 0.52% | 0.02% |
| Citric Acid | C$_6$H$_8$O$_7$ | 99.9% Citrate | 0.13% | 0.01% |
| Lignosulfonate | CaSalt | 50.0% Ca-Lig | 7.00% | 3.50% |
| Water | Nonchlorinated | | 10.20% | 10.20% |

The mites were the two spotted spider mite (*Tetranychus urticae* Koch) and the aphids were the peach aphid (*Myzus persicae*). The hosts were, respectively, marigold and chrysanthum.

Naturally infested plants were sprayed with a 1:5 dilution of the composition of Table 2 and water. A household plant mister was used to deliver equal volumes of water and of this solution to foliage undersides of test plants (ca. 5 ml/plant). A set of plants was left out as a complete control. Population counts were recorded 24 hours following treatment. Six leaves were randomly selected from top, middle and bottom portions of the plant (2 from each section) and infestation levels determined.

In Series A, there was no treatment. In Series B, water was used. In Series C the above solution was used.

RESULTS

MITE POPULATIONS:

| Treatment | 1 | 2 | 3 | 4 | 5 | 6 | 7 | 8 | 9 | 10 | Mean |
|---|---|---|---|---|---|---|---|---|---|---|---|
| Series A | 123 | 115 | 142 | 102 | 89 | 95 | 113 | 93 | 109 | 75 | a 106 |
| Series B | 73 | 97 | 105 | 84 | 90 | 72 | 63 | 88 | 69 | 57 | *b 80 |
| Series C | 2 | 7 | 7 | 3 | 5 | 1 | 0 | 2 | 5 | 2 | *c 3 |

Figures represent total numbers of two-spotted mites (all stages except eggs) per 6 randomly selected leaves. *=significantly different at the 5% level.

APHID POPULATIONS:

| Treatment | 1 | 2 | 3 | 4 | 5 | 6 | 7 | 8 | 9 | 10 | Mean |
|---|---|---|---|---|---|---|---|---|---|---|---|
| Compl Ck | 21 | 17 | 37 | 19 | 23 | 23 | 16 | 22 | 18 | 25 | a 22 |
| Ck | 16 | 24 | 26 | 18 | 31 | 24 | 17 | 19 | 20 | 23 | a 22 |
| BrSn | 0 | 0 | 0 | 1 | 0 | 0 | 0 | 0 | 0 | 0 | *b 0 |

Figures represent total numbers of peach aphids per 6 randomly selected leaves. *=significantly different at the 5% level.

Following is a discussion of ingredients of the soil treatment composition and of concentrations and rates of application.

As stated above the preferred pre-disposition substance is a water soluble lignosulfonate but other substances such as those listed above may be used. Also a mixture of any two or more of such substances may be used.

As stated above the predisposing substance together with other substances such as nutrients may be applied to soil in aqueous solution by sprinkling, by drip methods, or by injection in the soil followed by irrigation or by any other suitable method. It may also be applied in dry form and then infiltrated into the soil by irrigation.

Solutions may be applied in which the predisposing substance, e.g., lignosulfonate is present in concentrations of 10 or less to 50% or more by weight with other ingredients present in the proportions indicated by rates of application as discussed below.

Rates of application may be as follows in parts per million per acre foot of soil, although greater or lesser amounts may be used provided the predisposing substance is applied in amount sufficient to accomplish the intended result.

| Predisposing Substance | 50–1500 |
|---|---|
| Nitrogen | 10–150 |
| Phosphorus | 10–150 |
| Vitamin/co-factor | 5–100 |
| Microbes- | 2–50 grams per acre foot |

In addition potassium, zinc, manganese and iron may be included in amounts as follows in parts per acre foot of soil:

| Potassium | 10–150 |
|---|---|
| Zinc | 0.5–50 |
| Manganese | 0.5–50 |
| Iron | 0.5–50 |

In Table 1 above, molasses was used as a major component. It provides a nutrient source for soil microbes. Substitutes for molasses include various sugars, e.g., mannose, dextrose, lactose, cornsteed liquor, corn syrup and whey.

Suitable sources of nitrogen include urea, ammonium nitrate, calcium nitrate, potassium nitrate, ammonium sulfate, aqua ammonia, URAN, proteins, amino acids, and mixtures thereof.

Suitable sources of phosphorus include phosphoric acid, potassium phosphate, potassium pyrophosphate, ammonium phosphate nitrate, ammoniated triple superphosphate, ammoniated single superphosphate, ammonium phosphate, and mixtures thereof.

Suitable sources of potassium are potassium chloride, potassium sulfate, potassium gluconate, potassium acetate and potassium citrate, and mixtures thereof.

Suitable sources of zinc are zinc acetate, zinc sulfate, zinc benzoate, zinc chloride and zinc citrate, and mixtures thereof.

Suitable sources of manganese are manganese acetate, manganese chloride and manganese nitrate, and mixtures thereof.

Suitable sources of iron are ferric chloride, ferric sulfate, ferric citrate and ferric nitrate, and mixtures thereof.

It will be understood that a single substance, e.g., potassium phosphate, may provide a source of more than one nutrient.

Suitable vitamin/cofactor sources are yeast extract, thiamine pyrophosphate, riboflavin acetyl phosphate, biotin sulfoxide, pantothenic acid, phosphatidylcholine, inositol, PABA, nicotinic acid, folic acid, and mixtures thereof.

Suitable microbes include (1) fungi such as *Trichoderma viride, T. hamatum, T. harzianum, T. koningii, Penicillium oxalicum, P. funiculosum, P. urticae, P. vermiculatum, Gliocladium roseum, G. virens, Chaetomium globosum, Dactylella oviparasitica, Verticillium lacanii, Fusarium moniliforme var subglutinans, Arthrobotrys amerospora, A. conoides, Acremoniumboreale, A. falciforme, coniothyrium minitans*, and mixtures thereof and (2) bacteria such as *Pseudomonas fluorescens, Ps. putida, Enterobacter cloacae, Alcaligines spp., Arthrobacter citreus, A. globiformis, A. crystallopoietes, Bacillus subtilis, B. cereus, B. pumilus, B. mycoides, B. megaterium, Streptomyces griseus, S. aureofaciens*, and mixtures thereof.

It will, therefore, be apparent that a new and useful method of nematode control has been provided.

I claim:

1. A method of inhibiting the phytotoxic effect of soil borne pests or pathogens of the animal kingdom on plants grown in the soil which includes incorporating into the soil in which the plants are grown or are to be grown a composition which includes a water soluble lignosulfonate which is absorbed by said pests or pathogens and when so absorbed acts to render the pests or pathogens more susceptible to attack by soil microbes, said predisposing substance being applied at a rate of 50 to 1500 parts per million per acre foot of soil.

2. The method of claim 1 accompanied by incorporating in the soil microbiota which are effective to attack the pests or pathogens.

3. The method of claim 1 in which there are also incorporated in the soil nutrients for soil microbiota other than the lignosulfonate.

4. The method of claim 4 in which the added nutrients include nitrogen, phosphorus, and a vitamin co-factor.

5. The method of claim 5 in which the added nutrients include potassium, zinc, manganese, iron and a vitamin/cofactor.

6. The method of any one of claims 1 to 2 or 3 to 5 in which the soil is infested with nematodes and the crops grown in the soil are field crops, vegetable crops, fruit crops, nut crops or ornamental crops.

7. The method of claim 6 in which any other substance applied to the soil to promote or assist the effect of the predisposing substance is applied at a substantially smaller rate.

8. The method of claim 1 in which the soil is infested with nematodes.

9. The method of claim 1 in which the soil is retested with Daktulosphaira and is planted with grapes.

10. A method of inhibiting the phytotoxic effect of soil borne pests or pathogens of the animal kingdom on plants grown in the soil, said method comprising:

incorporating in the soil in which the plants are grown or are to be grown: (a) a composition which includes a water soluble lignosulfonate which is absorbed by such pests or pathogens and when so absorbed acts to render the pests or pathogens more susceptible to attack which is effective for the stated purpose but insufficient to have a substantial phytotoxic effect on plants grown in the soil, such composition containing no component in an amount which is phytotoxic when applied to the soil in the stated amount; and (b) soil microbiota which are effective to attack the pests or pathogens;

whereby the phytotoxic effect of soil borne pests or pathogens is inhibited.

11. A method of inhibiting the phytotoxic effect of soil borne pests or pathogens of the animal kingdom on plants grown in the soil, said method comprising:

incorporating in the soil in which the plants are grown or are to be grown: (a) a composition which includes a water soluble lignosulfonate which is absorbed by such pests or pathogens and when so absorbed acts to render the pests or pathogens more susceptible to attack which is effective for the stated purpose but insufficient to have a substantial phytotoxic effect on plants grown in the soil, such composition containing no component in an amount which is phytotoxic when applied to the soil in the stated amount;

whereby the phytotoxic effect of soil borne pests or pathogens is inhibited.

12. The method according to claim 11, wherein said method further comprises incorporating into said soil soil nutrients for soil microbiota other than lignosulfonate.

* * * * *